US012622728B2

(12) United States Patent
Delbressine et al.

(10) Patent No.: US 12,622,728 B2
(45) Date of Patent: May 12, 2026

(54) TRANSFER OF A PRETERM BABY FROM A NATURAL WOMB

(71) Applicant: TECHNISCHE UNIVERSITEIT EINDHOVEN, Eindhoven (NL)

(72) Inventors: Franciscus Leonardus Marie Delbressine, Eindhoven (NL); Tamara Hoveling, Eindhoven (NL); Marlou Monincx, Eindhoven (NL); Juliette Stephanie Van Haren, Eindhoven (NL); Guid Oei, Eindhoven (NL); Marieke Beatrijs Van Der Hout-Van Der Jagt, Eindhoven (NL)

(73) Assignee: TECHNISCHE UNIVERSITEIT EINDHOVEN, Eindhoven (NL)

( * ) Notice: Subject to any disclaimer, the term of this patent is extended or adjusted under 35 U.S.C. 154(b) by 341 days.

(21) Appl. No.: 18/028,402

(22) PCT Filed: Sep. 24, 2021

(86) PCT No.: PCT/NL2021/050578
§ 371 (c)(1),
(2) Date: Mar. 24, 2023

(87) PCT Pub. No.: WO2022/066014
PCT Pub. Date: Mar. 31, 2022

(65) Prior Publication Data
US 2023/0363792 A1     Nov. 16, 2023

(30) Foreign Application Priority Data

Sep. 24, 2020   (NL) ..................................... 2026534
Aug. 23, 2021   (NL) ..................................... 2029017

(51) Int. Cl.
*A61B 17/42*        (2006.01)
*A61G 11/00*        (2006.01)

(52) U.S. Cl.
CPC .............. *A61B 17/42* (2013.01); *A61G 11/00* (2013.01); *A61B 2503/02* (2013.01); *A61B 2503/40* (2013.01)

(58) Field of Classification Search
CPC .................. A61B 17/442; A61B 17/42; A61B 2017/00287; A61B 17/0293;
(Continued)

(56) References Cited

U.S. PATENT DOCUMENTS 4,018,230 A        4/1977  Ochiai et al.
4,875,482 A   *   10/1989  Hariri ................... A61B 17/42
                                                          606/122
(Continued)

FOREIGN PATENT DOCUMENTS

BE        863918 A        5/1978
CN     201578475 U        9/2010
CN     210932416 U        7/2020

OTHER PUBLICATIONS

Schvartzman, Javier A., et al. "Odon device for instrumental vaginal deliveries: results of a medical device pilot clinical study." Reproductive health 15.1 (2018): 1-10) (Year: 2018).*
(Continued)

*Primary Examiner* — Katherine M Shi
(74) *Attorney, Agent, or Firm* — Casimir Jones, S.C.; Robert A. Goetz

(57)            ABSTRACT

The present invention relates to a transfer assembly for transferring a preterm baby from a natural womb of a pregnant mammal to a transfer bag, comprising a base device having a pass-through opening configured to allow the preterm baby to pass through the base device, and wherein the base device is connected to a birth canal retractor, said birth canal retractor comprises a flexible sleeve disposed between the base device and an adjustable access ring, which retractor is to be inserted into the birth canal of the
(Continued)

pregnant mammal at least with the access ring thereof, and wherein the access ring is configured to be expanded or inflated while in the birth canal, wherein the assembly further comprising a transfer device comprising the transfer bag, said transfer bag being a flexible bag provided with an opening configured to allow the preterm baby to be received in the transfer bag, and wherein the opening is further provided with a coupling member, which coupling member is releasably secured to the base device, and wherein the transfer bag is provided with at least one integrated glove for receiving the hand of a medical practitioner in order to allow the transfer the preterm baby from the natural womb into the transfer bag.

13 Claims, 13 Drawing Sheets

(58) Field of Classification Search
CPC . A61B 2503/02; A61B 2503/40; A61G 11/00; A61G 11/009
See application file for complete search history.

(56) References Cited

U.S. PATENT DOCUMENTS

| | | | | |
|---|---|---|---|---|
| 5,632,750 | A * | 5/1997 | Alexander | A61B 17/442 606/1 |
| 2014/0330285 | A1 | 11/2014 | Rosenblatt et al. | |
| 2016/0074268 | A1 * | 3/2016 | Breegi | A61G 11/009 600/21 |

OTHER PUBLICATIONS

International Search Report & Written Opinion, International Patent Application No. PCT/NL2021/050578, mailed Jan. 24, 2022, 16 pages.

* cited by examiner

TRANSFER OF A PRETERM BABY FROM A NATURAL WOMB

TECHNICAL FIELD

The present invention relates to a transfer assembly for transferring a preterm baby from a natural womb of a pregnant mammal to a transfer bag. The present invention further relates to a kit-of-parts for assembling a transfer assembly. Also the present invention relates to a transfer device and/or a birth canal retractor for use in a transfer assembly of the present invention. An alternative transfer device is provided as well. Further, the present invention relates to a method for transferring a preterm baby from a natural womb of a pregnant mammal to a transfer bag.

BACKGROUND

Preterm birth, also known as premature birth, is the birth of a baby at fewer than 37 weeks gestational age, as opposed to full-term delivery at approximately 40 weeks. Very early preterm birth is before 32 weeks, early preterm birth occurs between 32-36 weeks, late preterm birth is between 34-36 weeks' gestation. The World Health Organization defines the following sub-categories of preterm birth, based on gestational age:

extremely preterm (less than 28 weeks);

very preterm (28 to 32 weeks); and moderate to late preterm (32 to 37 weeks).

In line with the various regulations and directives throughout the world, there is a common understanding that induction or caesarean birth should not be planned before 39 completed weeks unless medically indicated as premature infants are at greater risk for cerebral palsy, delays in development, hearing problems and problems with their vision. The earlier a baby is born, the greater these risks will be.

However, despite this common understanding, spontaneous preterm birth may occur as well as the induction of labour or caesarean required for other medical reasons. There may be certain medical reasons for early delivery such as preeclampsia. Also, in view of the recent COVID-19 pandemic medical necessity for caesarean birth is more likely to occur in order to allow a pregnant woman to be intubated without having a direct negative effect on the foetus.

Preterm birth is the most common cause of death among infants worldwide. About 15 million babies are preterm each year (5% to 18% of all deliveries). Late preterm birth accounts for 75% of all preterm births. This rate is inconsistent across countries. In the United Kingdom 7.9% of babies are born pre-term and in the United States 12.3% of all births are before 37 weeks gestation. Approximately 0.5% of births are extremely early periviable births (20-25 weeks of gestation), and these account for most of the deaths. In many countries, rates of premature births have increased between the 1990s and 2010s. Complications from preterm births resulted in 0.81 million deaths in 2015, down from 1.57 million in 1990. The chance of survival at 22 weeks is about 6%, while at 23 weeks it is 26%, 24 weeks 55% and 25 weeks about 72%. The chances of survival without any long-term difficulties are lower.

Given the significant low survival rates of preterm birth, there is a need to develop procedures increasing the survival rates of preterm birth.

DESCRIPTION OF THE INVENTION

In order to increase the survival rate of a preterm birth, in particular extremely preterm birth, the present invention provides hereto a transfer assembly for transferring a preterm baby from a natural womb of a pregnant mammal to a transfer bag. By providing such a transfer assembly, the preterm baby can be transferred, or transported by using the transfer bag, to an artificial womb to let the prematurely born child extend its stay. To let the child develop further in the artificial womb, a safe transfer from the natural womb to an artificial womb is now provided by the present invention.

It is stressed that the artificial womb and the transfer assembly according to the present invention for transferring the preterm baby to the artificial womb is intended to be used only in case of spontaneous preterm birth or induction of labour or caesarean required for other medical reasons in order to increase the survival rate of the preterm baby. By transferring a preterm baby from the natural womb to an artificial womb using the transfer assembly of the present invention, direct contact between the ambient environment (i.e. containing oxygen) and the preterm baby is herewith prevented. Thus optimizing and extending the ideal situation for the preterm baby, in particular for the lungs of the preterm baby, to further develop in a womb-like surrounding.

Although one could argue that by providing the transfer assembly (including a transfer bag) according to the present invention and the eventual transfer of the preterm baby to an artificial womb, the transfer of the perinate from the natural womb to an artificial womb cannot qualify as giving birth. However, although the perinate is not in direct contact with the ambient environment (i.e. containing oxygen) and thus may (legally) considered not wholly brought into the world as such (as a self-breathing human being), in view of the present invention the transfer of the perinate from the natural womb classifies as giving birth (either via a caesarean section or via the birth canal). As a consequence, by transferring the perinate from the natural womb, the perinate classifies, according to the invention, as a preterm baby.

As used herein, the term "preterm baby" refers to the perinate (or foetus) comprised in the natural womb which needs to be delivered prematurely, i.e. before 37 weeks gestation, due to spontaneous (preterm) delivery or due to induced labour or caesarean section as required in case of a medical necessity. The term "preterm baby" further refers to any birth before 37 weeks gestation, also including extremely early periviable births (20-25 weeks gestation). Unless indicated otherwise, the term "preterm baby" includes extremely preterm (less than 28 weeks), very preterm (28 to 32 weeks), and moderate to late preterm (32 to 37 weeks). Other synonyms for the term "preterm baby" as used herein may include perinate or infant. Although not always correct, the term "preterm baby" may considered to be similar to the term "incubator baby", i.e. an infant of which the vital organs needs to be developed further after birth.

As used herein, the term "artificial womb" may refer to a natural womb-mimicking device, wherein the preterm baby transferred from the natural womb may be develop further. In order to avoid any further interference, the umbilical cord of the preterm baby transferred into the artificial womb needs to be connected to an artificial placenta in order to allow (the vital organs of) the preterm baby to further develop. Synonyms for the term "artificial womb" include "preterm life support system", "liquid based life support system" and "perinatal life support system".

Also, as used herein, the term "pregnant mammal" may refer to a human being carrying a baby before giving birth to that baby. On the other hand, the term "pregnant mammal" may also refer to an animal, i.e. a mammal, wherein such animal is viviparous.

Further, as used herein, the terms "transferring" and "transfer" refer to the active step of transporting, moving, conveying or removing something from one place to another place. In the present invention the terms "transferring" and "transfer" refer to the movement of a preterm baby from its natural, original position in the natural womb of a pregnant mammal to another, in this case artificial, environment.

The present invention relates, in particular, to the transfer of a preterm baby from the natural womb to a transfer bag wherein the preterm baby is delivered via the birth canal. In other words, the present invention does not relate to the transfer of a preterm baby from the natural womb to a transfer bag wherein the preterm baby is delivered via a caesarean procedure.

In order to assist the transfer of a preterm baby from the natural womb to a transfer bag, wherein the preterm baby is delivered via the birth canal, the present invention provides hereto a transfer assembly comprising at least the following parts:

a transfer device comprising a transfer bag for transferring the preterm baby transferred from the natural womb to an artificial womb;

a birth canal retractor for assisting the transfer of the preterm baby from the natural womb to the transfer device; and a base device providing a reliable connection between the transfer device and the birth canal retractor.

By providing the transfer assembly of the present invention, a smooth and seamless transfer of the preterm baby from the natural womb into the transfer bag can be guaranteed wherein any involvement of ambient conditions during delivery is prevented. In other words, the present invention provides for an assisted delivery via the natural birth canal wherein the preterm baby transferred from the natural womb does not come into contact with ambient conditions, such as oxygen containing air. Even further, by providing the transfer assembly of the present invention, the preterm baby will not be influenced by external factors, such as change in light intensity, ambient air pressure, temperature fluctuations of the (artificial) amniotic fluid, and the like.

The different parts of the transfer assembly to assist the transfer of a preterm baby from the natural womb, via the birth canal, to an artificial environment, such as a transfer bag are further described below.

Birth Canal Retractor

The transfer assembly to assist the transfer of a preterm baby from the natural womb, via the birth canal, to an artificial environment comprises a birth canal retractor in order to avoid any interaction between the preterm baby and the birth canal and in order to provide a connection between the natural womb and the artificial environment, such as a transfer bag which connection is able to contain (artificial) amniotic fluid. In order to provide such a protective connection, the birth canal retractor of the present invention comprises a flexible sleeve disposed in a cylindrical configuration between a first open end and a second open end, which second open end is provided with a diameter adjustable access ring.

The birth canal retractor is arranged to be inserted into the birth canal of the pregnant mammal at least with the access ring thereof. The access ring is configured to increase in diameter, e.g. automatically or manually, while in the birth canal such that the access ring eventually provides an access (in case of sufficient cervical dilation) for the preterm baby to the birth canal retractor through the access ring. The access ring may be expanded or inflated while in the birth canal, thereby providing an access for the preterm baby to the birth canal retractor.

In an embodiment of the present invention the access ring may be an inflatable ring. In case of such an inflatable ring, the ring preferably comprises an inlet for supplying a medium, such as a gas (e.g. air) or a liquid (e.g. water or artificial amniotic fluid) to the ring in order to inflate the ring while in the birth canal. In addition, the inflatable ring may comprise an outlet or valve to release any medium from the ring in order to deflate the ring, e.g. before removal of the birth canal retractor from the birth canal. However, deflation of the ring may also provided by discharging any medium via the inlet of the inflatable ring.

In another embodiment the access ring may be an expandable ring. In case of such expandable ring, the ring is preferably provided in folded form, preferably in folded biased form, before inserting the birth canal retractor into the birth canal. After positioning the birth canal retractor in the birth canal, the folded ring may unfold in order to increase the diameter of the access ring. The unfolding of such expandable access ring may be facilitated by providing an external force by, for example, the medical practitioner. However, the unfolding may also be facilitated by cervical dilation reducing the pressure applied to the folded access ring, thus automatically unfolding the access ring during the natural process of cervical dilation.

Although the dimensions of the access ring should be chosen such that in the unexpanded state of the access ring the birth canal retractor can be inserted in the birth canal, preferred dimensions of the access ring in the unexpanded state are between 2 cm to 7 cm. Also, although the dimensions of the access ring should be chosen such that in the expanded state of the access ring a preterm baby should be allowed to access the birth canal retractor from the natural womb, preferred dimensions of the access ring in the expanded state are between 6 cm to 14 cm.

Further to the above, the first open end of the birth canal retractor is preferably configured to connect to the base device. In order to provide such a connection the first open end of the birth canal retractor may be provided with a thickened ring. Such thickened ring may cooperate with a circumferential groove provided in the base device to provide a reliable and water-tight sealed connection between the birth canal retractor and the base device. Alternatively, in an embodiment of the present invention the first open end of the birth canal retractor is connected to the base device in order to provide one integral birth canal retractor device.

Regarding the flexible sleeve of the birth canal retractor, it is noted that the length of such a flexible sleeve may closely resemble the length of the birth canal, e.g. about 6 cm to 15 cm. Alternatively, the access ring of the birth canal retractor may have a width which corresponds or closely resembles the length of the birth canal.

The birth canal retractor may be inserted manually by the medical practitioner, wherein at least the access ring is inserted and positioned abutting the cervix and/or enclosing the fornix of the uterus. Alternatively, the birth canal retractor may be inserted by using a inserting device, which inserting device is configured to receive the access ring in unexpanded state and to release the access ring while inserted in the birth canal.

It is noted that before placing the birth canal retractor in the birth canal, lavage of the birth canal of the pregnant mammal is preferably performed in order to avoid any contamination of the access ring or any other interior part of the birth canal retractor. Also, as the medical practitioner is still able to (manually) monitor the cervical dilation of the pregnant mammal after insertion of the birth canal retractor, lavage of the interior of the birth canal retractor may be performed before assembling the transfer assembly, i.e. connecting the transfer device to the birth canal retractor device, and supplying artificial amniotic fluid to the interior of the birth canal retractor.

Base Device

The transfer assembly to assist the transfer of a preterm baby from the natural womb, via the birth canal, to an artificial environment comprises a base device in order to connect the birth canal retractor to a transfer device comprising a transfer bag. The base device of the present invention comprises a base body provided with an annular shaped pass-through opening, wherein the pass-through opening is configured to allow the preterm baby to pass through the base device. Although the dimensions of such pass-through opening should be chosen such that the preterm baby is allowed to pass through, it is further noted that the dimensions of the pass-through opening should be selected such that the hand of a medical practitioner is also able to pass-through the opening. As such the diameter of the pass-through opening is preferably selected in the range of 10 cm to 20 cm.

As already provided above, the base body of the base device may be configured to receive the first open end of the birth canal retractor. In an embodiment of the present invention, the base body of the base device may be provided with receiving means, such as a circumferential groove, for receiving the first open end of the birth canal retractor. Alternatively, the base body of the base device may be rigidly connected to the birth canal retractor in order to form one integral birth canal retractor device.

In order to releasably secure a transfer device to the base device, the base body of the base device may be provided with securing means. Suitable securing means may include a bayonet connection, threaded connection, or clip connection. In addition to the suitable securing means, other sealing means may be present in the base body of the base device and/or the coupling member of the transfer device. Suitable sealing means may include a circumferential flexible O-rings and/or a circumferential labyrinth closure, preferably provided in a recess of the coupling member or base body.

Although the base body of the base device may have any suitable form, an annular form similar to the annular form of the pass-through opening provided in the base body is preferred. In addition, the base body is preferably rigid in order to provide a reliable and solid connection between the base device and the transfer device.

Transfer Device

The transfer assembly to assist the transfer of a preterm baby from the natural womb, via the birth canal, to an artificial environment comprises a transfer device comprising a transfer bag for receiving the preterm baby transferred from the natural womb. The transfer bag of the present invention is a flexible bag provided with an annular shaped receiving opening. The dimensions of the receiving opening are chosen such as to allow the preterm baby to be received in the transfer bag. In addition the volume of the transfer bag may be selected such as to mimic the volume of the natural womb wherefrom the preterm baby is transferred. Preferred volumes of the transfer bag are within the range of 800 mL to 3000 mL.

The transfer bag of the present invention is provided with at least one integrated glove for receiving the hand of a medical practitioner, in particular a gynaecologist, in order to allow the medical practitioner to access the natural womb and to allow facilitated transfer of the preterm baby from the natural womb into the transfer bag. Preferably the integrated glove is positioned opposite to the receiving opening of the transfer bag.

The receiving opening of the transfer bag of the present invention is further provided with a coupling member for releasably coupling the transfer device to the base device. In a preferred embodiment the coupling member is an annular shaped coupling member corresponding to the annular shaped receiving opening of the transfer bag. Even further, the coupling member may be in the form of a solid rigid ring for providing a secured and reliable coupling between the transfer device and the base device. It is noted that the dimensions of the receiving opening are preferably chosen such that they closely resembles the dimensions of the pass-through opening provided in the base body of the base device, i.e. in the range of between 10 cm to 20 cm.

The transfer device of the present invention may further be provided with an inlet for supplying a liquid, such as an artificial amniotic fluid (AAF), to the interior of the transfer device. Obviously, during use, by providing a liquid to the interior of the transfer device, the supply of the liquid is automatically extended to the interior of the base device and the birth canal retractor. Further, the transfer device may further be provided with a valve, e.g. an air vent, for releasing air from the transfer device. Such release of air via a valve is highly preferred in case the transfer assembly is supplied with liquid. In use, the transfer assembly comprises one main opening, i.e. the opening facing the natural womb formed by the access ring. Pressure build-up in the transfer assembly (by supplying liquid to the transfer assembly) will negatively effect the abutment of the access ring to the cervix in case no air valve is provided.

In a further embodiment, the transfer bag may be provided with an integrated closure in the vicinity of the receiving opening, such as an integrated wire, to close the receiving opening of the transfer bag after the preterm baby is received in the transfer bag. In order to avoid accidental squeezing of the umbilical cord of the preterm baby, the closure of the receiving opening of the transfer bag is facilitated by loosely securing the integrated closure around the umbilical cord connected to the preterm baby.

Once the baby is received in the transfer bag, the transfer device may be released from the base device. In order to further process the transfer of the preterm baby to a further artificial environment, such as an artificial womb, the transfer bag is preferably placed on a horizontal plane such that the receiving opening of the transfer bag is facing upwards away from the horizontal plane.

Aspects of the Present Invention

In a first aspect of the present invention, the present invention relates to a transfer assembly for transferring a preterm baby from a natural womb of a pregnant mammal to a transfer bag, the assembly comprising:

a base device comprising an annular shaped pass-through opening having a central axis, wherein the pass-through opening is configured to allow the preterm baby to pass through the base device, and wherein the base device further comprises a womb facing side and a transfer bag facing side; and a transfer device comprising the transfer bag, said transfer bag being a flexible bag provided with an annular shaped receiving opening having a central axis, wherein the receiving opening is configured to allow the preterm baby to be received in the transfer bag, and wherein the receiving opening is further provided with a coupling member, which coupling member is releasably secured to the transfer bag facing side of the base device in such configuration that the central axis of said pass-through opening coincides with the central axis of said receiving opening.

In the transfer assembly of the present invention, the womb facing side of the base device is connected to a birth canal retractor. The birth canal retractor comprises a flexible sleeve disposed in a cylindrical configuration between the womb facing side of the base device and a diameter adjustable access ring, wherein the birth canal retractor is arranged to be inserted into the birth canal of the pregnant mammal at least with the access ring thereof. Further, in the transfer assembly of the present invention, the access ring is configured to be expanded or inflated while in the birth canal, thereby providing an access for the preterm baby to the transfer assembly through the access ring in an expanded or inflated state of the access ring.

In this first aspect of the present invention, the transfer bag is provided with at least one integrated glove for receiving the hand of a medical practitioner, in particular a gynaecologist, in order to allow the medical practitioner to transfer the preterm baby from the natural womb into the transfer bag.

The womb facing side of the base device and the birth canal retractor may form one integral birth canal retractor device. The birth canal retractor may be arranged to be inserted into the birth canal of the pregnant mammal at least with the access ring and a substantial part of the flexible sleeve.

The base device and/or the transfer device may further comprise an inlet for supplying a liquid, preferably artificial amniotic fluid (AAF), to the interior of the transfer assembly. In addition, the base device and/or the transfer device may be further provided with an outlet (such as a valve) to release liquid and/or gas (such as air) from the transfer assembly to the exterior, e.g. ambient environment.

In the transfer assembly of the present invention, the integrated glove may be positioned opposite to the receiving opening of the transfer bag. In addition, the transfer bag may further comprise an integrated closure in the vicinity of the receiving opening, such as an integrated wire, to close the receiving opening of the transfer bag after the preterm baby is received in the transfer bag, wherein the closure of the receiving opening of the transfer bag is facilitated by loosely securing the integrated closure around the umbilical cord connected to the preterm baby.

In a second aspect of the present invention, the present invention relates to a kit-of-parts for assembling the transfer assembly for transferring a preterm baby from a natural womb of a pregnant mammal to a transfer bag, the kit-of-parts comprising:

a base device comprising an annular shaped pass-through opening having a central axis, wherein the pass-through opening is configured to allow the preterm baby to pass through the base device, and wherein the base device further comprises a womb facing side and a transfer bag facing side; and a transfer device comprising the transfer bag, said transfer bag being a flexible bag provided with an annular shaped receiving opening having a central axis, wherein the receiving opening is configured to allow the preterm baby to be received in the transfer bag, and wherein the receiving opening is further provided with a coupling member, which coupling member is configured to be releasably secured to the transfer bag facing side of the base device in such configuration that the central axis of said pass-through opening coincides with the central axis of said receiving opening.

The transfer bag comprised in the kit-of-parts of the present is further provided with at least one integrated glove for receiving the hand of a medical practitioner, in particular a gynaecologist, in order to allow the medical practitioner to transfer the preterm baby from the natural womb into the transfer bag.

In addition to the above, the kit-of-parts may further comprise a birth canal retractor configured to be connected to the womb facing side of the base device, said birth canal retractor comprises a flexible sleeve disposed in a cylindrical configuration between a first open end connectable to the womb facing side of the base device and a second open end provided with a diameter adjustable access ring, wherein the birth canal retractor is arranged to be inserted into the birth canal of the pregnant mammal at least with the access ring thereof.

The access ring of the birth canal retractor is preferably configured to be expanded or inflated while in the birth canal, thereby providing an access for the preterm baby to the transfer assembly through the access ring in an expanded or inflated state of the access ring.

Alternatively, the kit-of-parts may further comprise a birth canal retractor connected to the womb facing side of the base device, said birth canal retractor comprises a flexible sleeve disposed in a cylindrical configuration between the womb facing side of the base device and a diameter adjustable access ring, wherein the birth canal retractor is arranged to be inserted into the birth canal of the pregnant mammal at least with the access ring thereof, and wherein the access ring is configured to be expanded or inflated while in the birth canal, thereby providing an access for the preterm baby to the transfer assembly through the access ring in an expanded or inflated state of the access ring.

In a third aspect of the present invention, the present invention relates to a transfer device for use in a transfer assembly for transferring a preterm baby from a natural womb of a pregnant mammal to a transfer bag according to the first aspect of the present invention, wherein the transfer device comprises a transfer bag, said transfer bag being a flexible bag provided with an annular shaped receiving opening, wherein the receiving opening is configured to allow the preterm baby to be received in the transfer bag, wherein the receiving opening is further provided with a coupling member, and wherein the transfer bag is provided with at least one integrated glove for receiving the hand of a medical practitioner, in particular a gynaecologist, in order to allow the medical practitioner to transfer the preterm baby from the natural womb into the transfer bag.

The transfer device may further comprise an inlet for supplying a liquid, preferably artificial amniotic fluid (AAF), to the interior of the transfer assembly. In addition, the base device and/or the transfer device may be further provided with an outlet (such as a valve) to release liquid and/or gas (such as air) from the transfer assembly to the exterior, e.g. ambient environment. In addition, the integrated glove may be positioned opposite to the receiving opening of the transfer bag.

In this third aspect of the present invention, the transfer bag may further comprise an integrated closure in the vicinity of the receiving opening, such as an integrated wire, to close the receiving opening of the transfer bag after the preterm baby is received in the transfer bag, wherein the closure of the receiving opening of the transfer bag is facilitated by loosely securing the integrated closure around the umbilical cord connected to the preterm baby.

In a fourth aspect of the present invention, the present invention relates to a birth canal retractor for use in a transfer assembly for transferring a preterm baby from a natural womb of a pregnant mammal to a transfer bag according to the first aspect of the present invention, wherein the birth canal retractor comprises a flexible sleeve disposed in a cylindrical configuration between a first open end and a second open end provided with a diameter adjustable access ring, wherein the birth canal retractor is arranged to be inserted into the birth canal of the pregnant mammal at least with the access ring thereof, and wherein the access ring is configured to be expanded or inflated while in the birth canal, thereby providing an access for the preterm baby to the birth canal retractor through the access ring in an expanded or inflated state of the access ring.

The first open end may be connected to a base device comprising an annular shaped pass-through opening, wherein the pass-through opening is configured to allow the preterm baby to pass through the base device.

In a fifth aspect of the present invention, the invention relates to a method for transferring a preterm baby from a natural womb of a pregnant mammal to a transfer bag, the method comprising the steps of:

i) providing a kit-of-parts according to the second aspect of the present invention;

ii) providing an pregnant mammal;

iii) performing lavage of the birth canal of the pregnant mammal;

iii) inserting the birth canal retractor connected to the base device into the birth canal of the pregnant mammal at least with the access ring thereof;

iv) monitoring the cervical dilation of the pregnant mammal and simultaneously increasing the diameter of the access ring while in the birth canal such that it eventually provides an access for the preterm baby to the transfer assembly;

v) in case sufficient cervical dilation is observed, releasably securing the transfer device to the base device to form a transfer assembly;

vi) supplying a liquid, preferably artificial amniotic fluid (AAF), to the interior of the transfer assembly;

vii) allowing a medical practitioner, in particular a gynaecologist, to access the natural womb by hand using the integrated glove provided in the transfer bag; and viii) transferring the preterm baby from the natural womb into the transfer bag.

In addition, the transfer bag may comprise an integrated closure in the vicinity of the receiving opening, wherein the method further comprises the step of:

closing the opening of the transfer bag by loosely securing the integrated closure of the transfer bag around the umbilical cord connected to the preterm baby.

After receiving the preterm baby from the natural womb into the transfer bag, the method may further comprise the step of:

releasing the transfer device from the base device and placing the transfer bag on a horizontal plane such that the receiving opening of the transfer bag is facing upwards away from the horizontal plane.

Alternative Embodiment

In addition to the embodiments and aspects provided above, the present invention further discloses an alternative transfer device for transferring a preterm baby from a natural womb of a pregnant mammal to a transfer bag. In this sixth aspect of the present invention, the alternative transfer device comprises:

a base body;

an expandable access ring; and the transfer bag being a flexible bag arranged between the base body and the ring, wherein the flexible bag is configured to receive the preterm baby.

The transfer device according to this alternative embodiment is arranged to be inserted into a birth canal at least with the access ring thereof. The access ring is configured to be expanded while in the birth canal, thereby providing an access for the baby to the bag through the access ring in an expanded state of the access ring. Even further, the access ring is configured to be contracted when the preterm baby has been received in the bag, thereby enclosing the preterm baby in the bag.

In accordance with the transfer device according to the sixth aspect of the invention, wherein the expandable ring is configured to be contracted when the baby has been received in the bag, thereby enclosing the baby in the bag, preferably the contraction of the expandable ring is such that umbilical cord blood flows are protected from occlusion.

In this alternative embodiment of the present invention, the transfer bag is preferably a double-layer bag, and wherein the device has an inlet for providing a gas, preferably sterilized air, between the two layers of the bag.

In order to facilitate insertion of the transfer device into the birth canal, the transfer bag has preferably a collapsed state, and an expanded state for receiving the baby, wherein the device is configured to allow the bag to expand from its collapsed state into the expanded state as a result of retracting the base body from the birth canal, while the ring is in its expanded state in the birth canal.

The base body of this alternative embodiment of the present invention has preferably an inlet for providing a liquid, preferably artificial amniotic fluid (AAF), into the bag. In addition, the expandable access ring may be an inflatable ring.

In a further aspect of the alternative embodiment of the present invention, the seventh aspect of the present invention relates to a method for transferring a preterm baby from a natural womb of a pregnant mammal to a transfer bag, using the transfer device according to the alternative embodiment of the present invention, wherein the method comprises the steps of:

a) inserting the transfer device into a birth canal at least with the expandable access ring thereof;

b) expanding the access ring while in the birth canal such that it provides an access for the baby into the bag;

c) allowing the baby to move into the bag, passing through the access ring;

d) contracting the access ring when the baby has been received in the bag; and e) removing the device containing the baby in the bag from the birth canal.

For the purpose of step c), the base body may be retracted from the birth canal, thereby creating an under pressure in the bag. Even further, during pulling of the base body from the birth canal, artificial amniotic fluid may be inserted into the bag.

The transfer device according to the sixth aspect of the present invention may be equipped with a monitoring module, such as including an optical sensor, at the tip of the base body, that is, at the end of the base body where the ring is located and which faces towards the baby during use. As a result, a condition inside the bag and/or a condition of the baby may be monitored.

EXAMPLES

The present invention will be further described by way of example only with reference to the accompanying drawings, in which.

Figure 1:
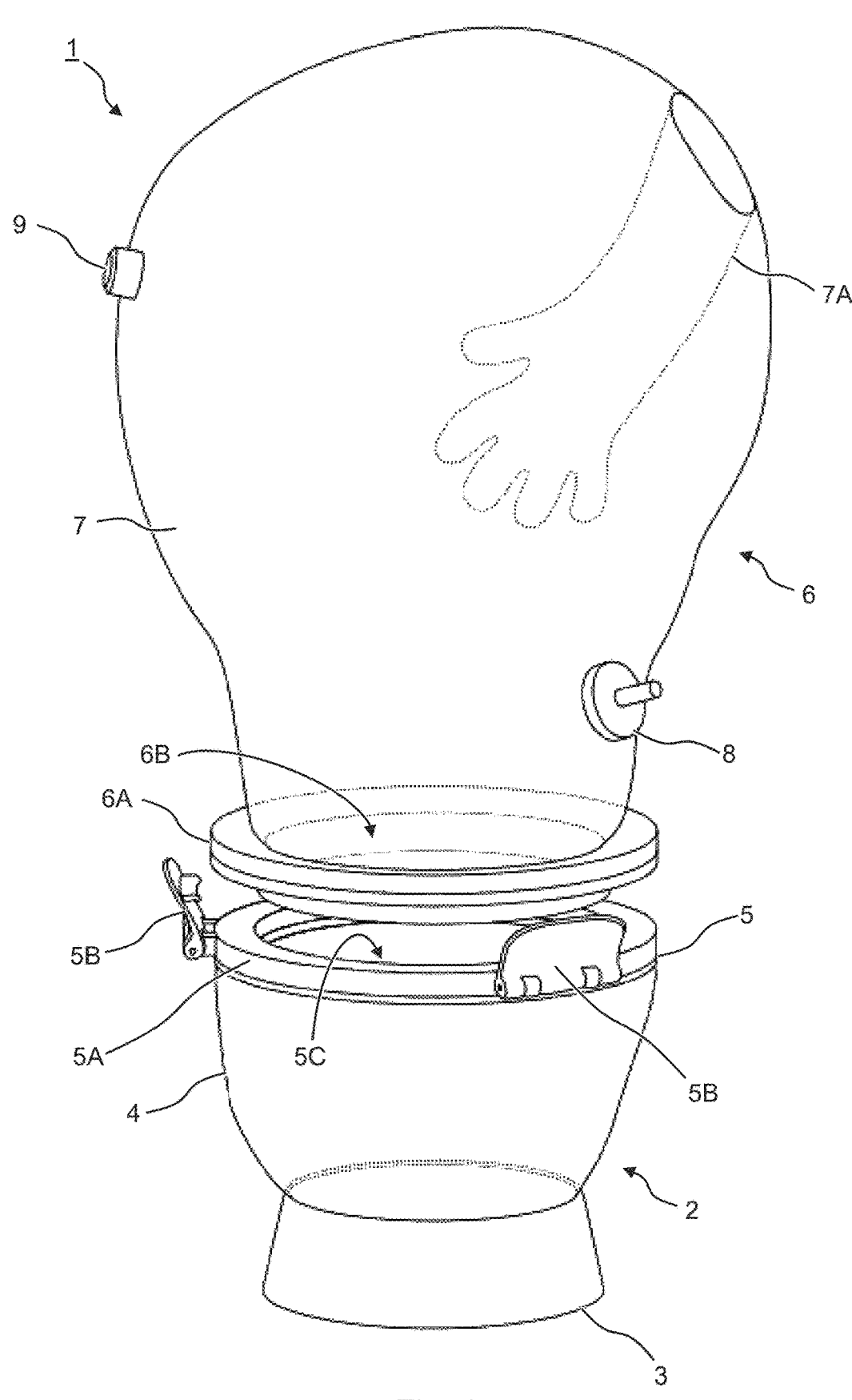
FIG. 1 shows the different parts of the transfer assembly of the first aspect of the invention.

FIG. 1 shows a transfer assembly 1 according to the present invention comprising an birth canal retractor 2 (also referred to as an inflatable retractor) comprising an inflatable insertion ring or retractor ring 3 (also referred to as the access ring) connected to the retractor sleeve 4. The insertion ring 3 as shown in FIG. 1 is inflatable in order to increase the diameter of the opening provided by the insertion ring 3 and to allow access of the preterm baby (not shown) in the natural womb (not shown) to the birth canal retractor 2.

The retractor sleeve 4 of the birth canal retractor 2 is further connected at its other end to the base device 5. The base device 5 as shown in FIG. 1 comprises a rigid ring 5A (also referred to as the base body) provided with clips 5B in order to releasably secure the base device 5 to the transfer device 6. The base body 5A is provided with a pass-through opening 5C with a sufficient diameter in order to allow the preterm baby (not shown) to pass-through the base device 5 into the transfer device 6 and in order to allow the medical practitioner (not shown) to monitor the progress of the delivery (cervical dilation) and to guide the preterm baby through the transfer assembly 1 into the transfer device 6.

The transfer device 6 is provided with a flexible transfer bag 7 provided with a glove 7A to receive the hand of the medical practitioner (not shown). The transfer bag 7 is further provided with a supply 8 for supplying artificial amniotic fluid to the interior of the transfer bag 7 and, subsequently, the complete transfer assembly 1. As shown in FIG. 1, the supply 8 might also be used as a drain for draining artificial amniotic fluid from the interior of the transfer assembly 1. Further, as shown in FIG. 1, the transfer bag 7 is provided with an air valve 9 to release air from the transfer bag 7 in case of supplying artificial amniotic fluid to the interior of the transfer bag 7.

The transfer device 6 is further provided with a coupling member 6A, which coupling member 6A has similar dimensions as the base device 5. The coupling member 6A is depicted in FIG. 1 as a rigid ring which allows connection to the base device 5. In particular the opening 6B provided in the coupling member 6A cooperates with the opening 5C provided in the base body 5A.

Figure 2:
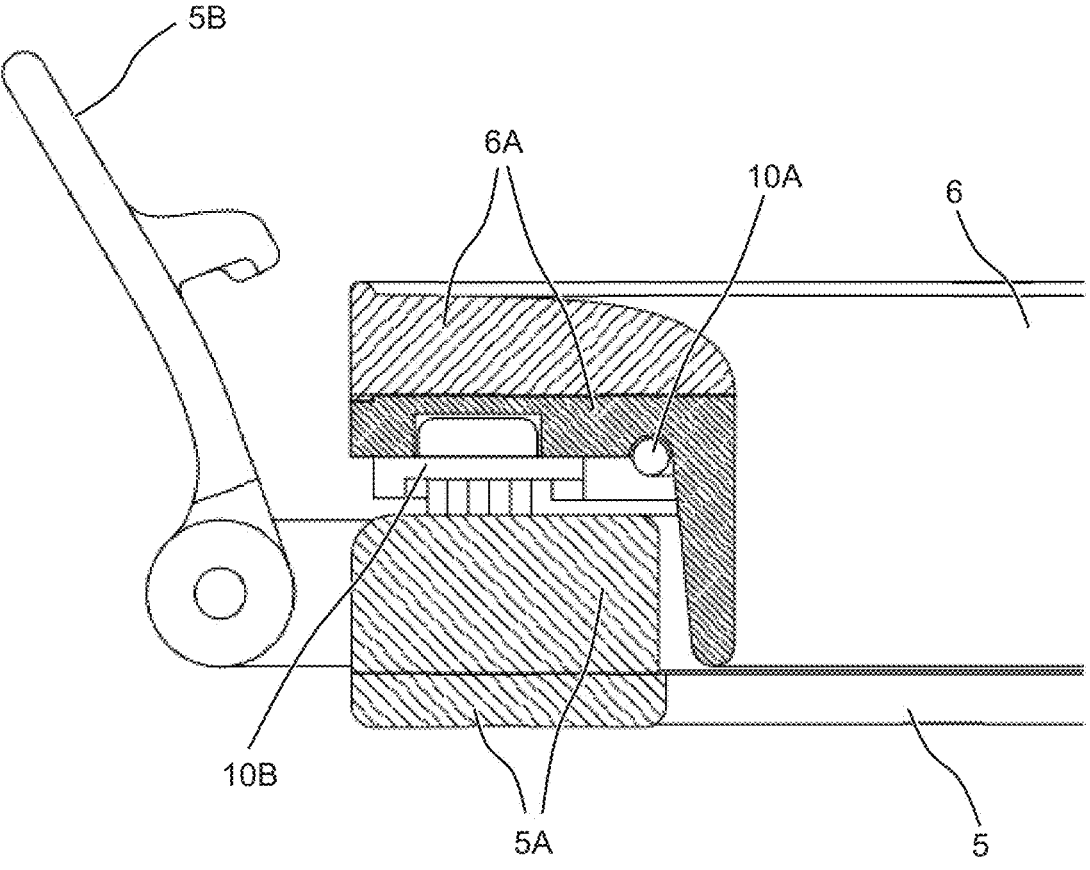
FIG. 2 is a cross-sectional view of a part of the connection between the base device and the transfer device.
Figure 3A:
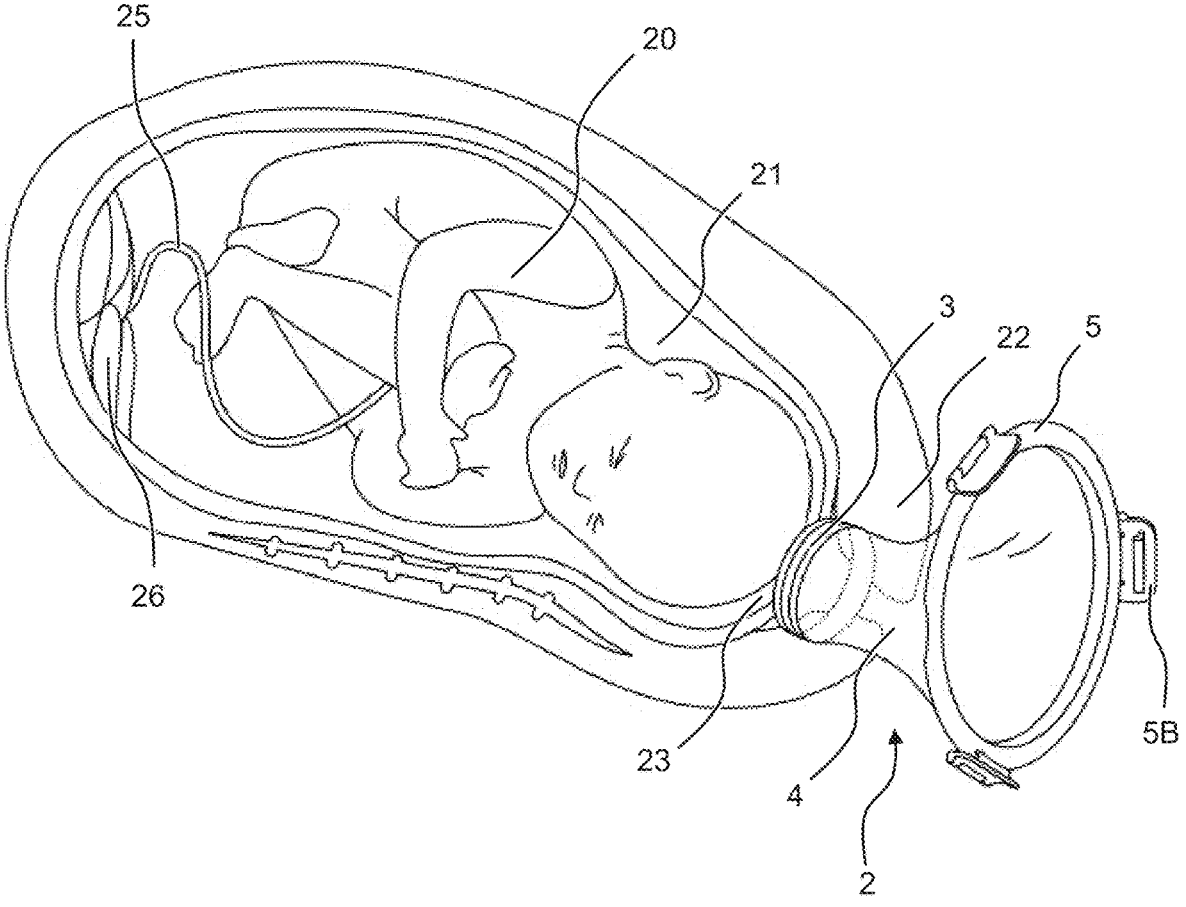
FIG. 3 depicts the method of transferring a preterm baby from the natural womb into the transfer bag according to the fifth aspect of the invention.
Figure 3B:
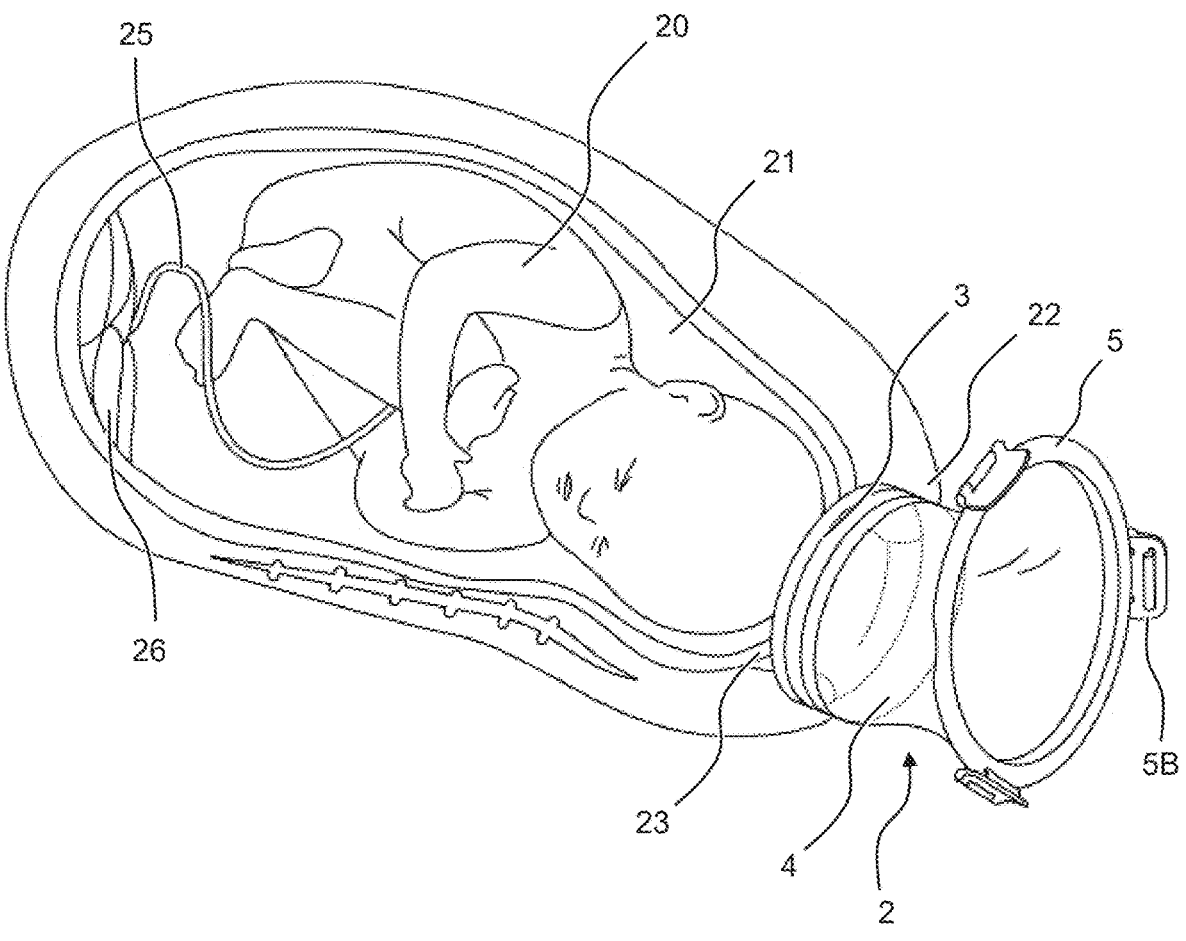
Figure 3C:
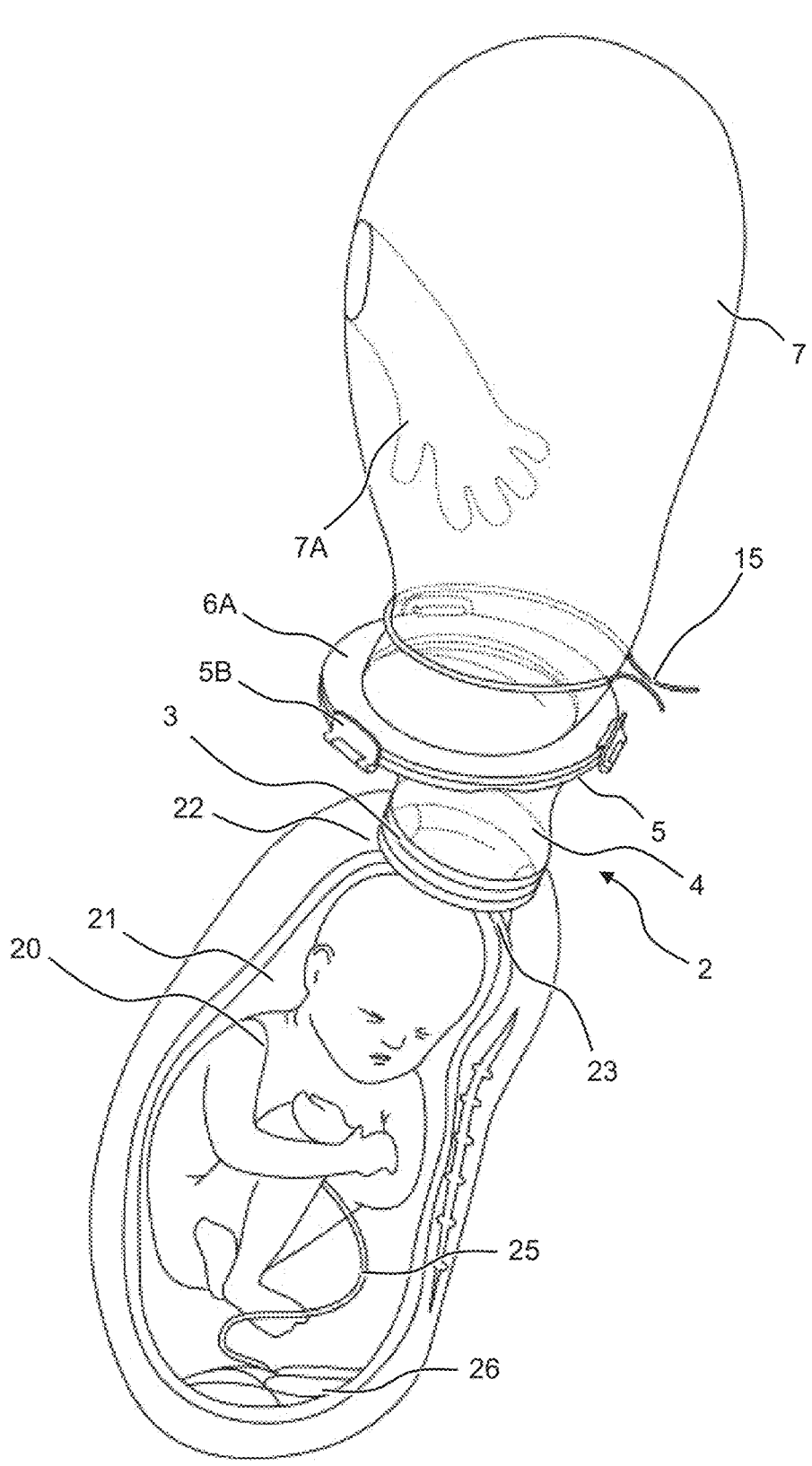
Figure 3D:
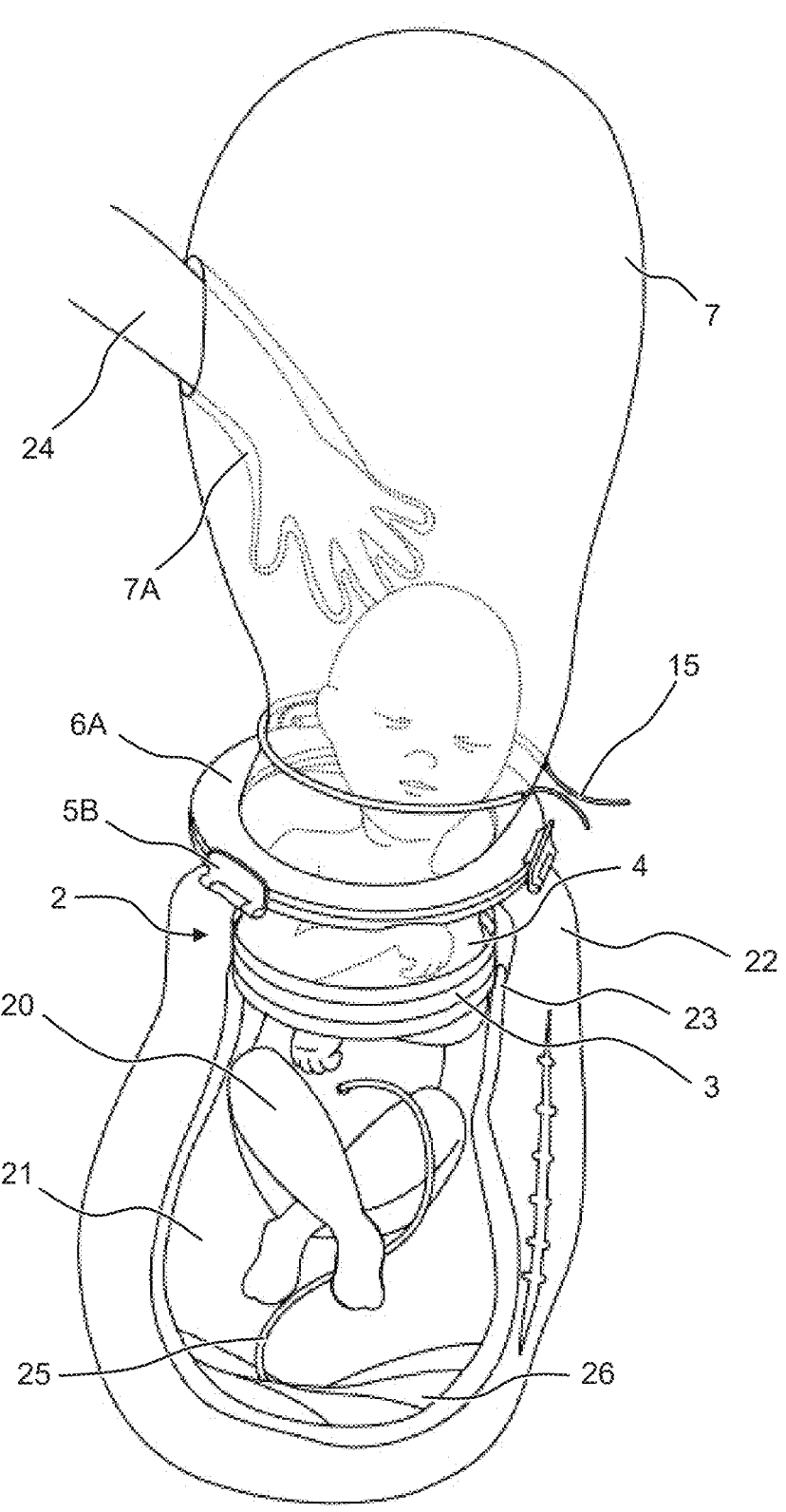
Figure 3E:
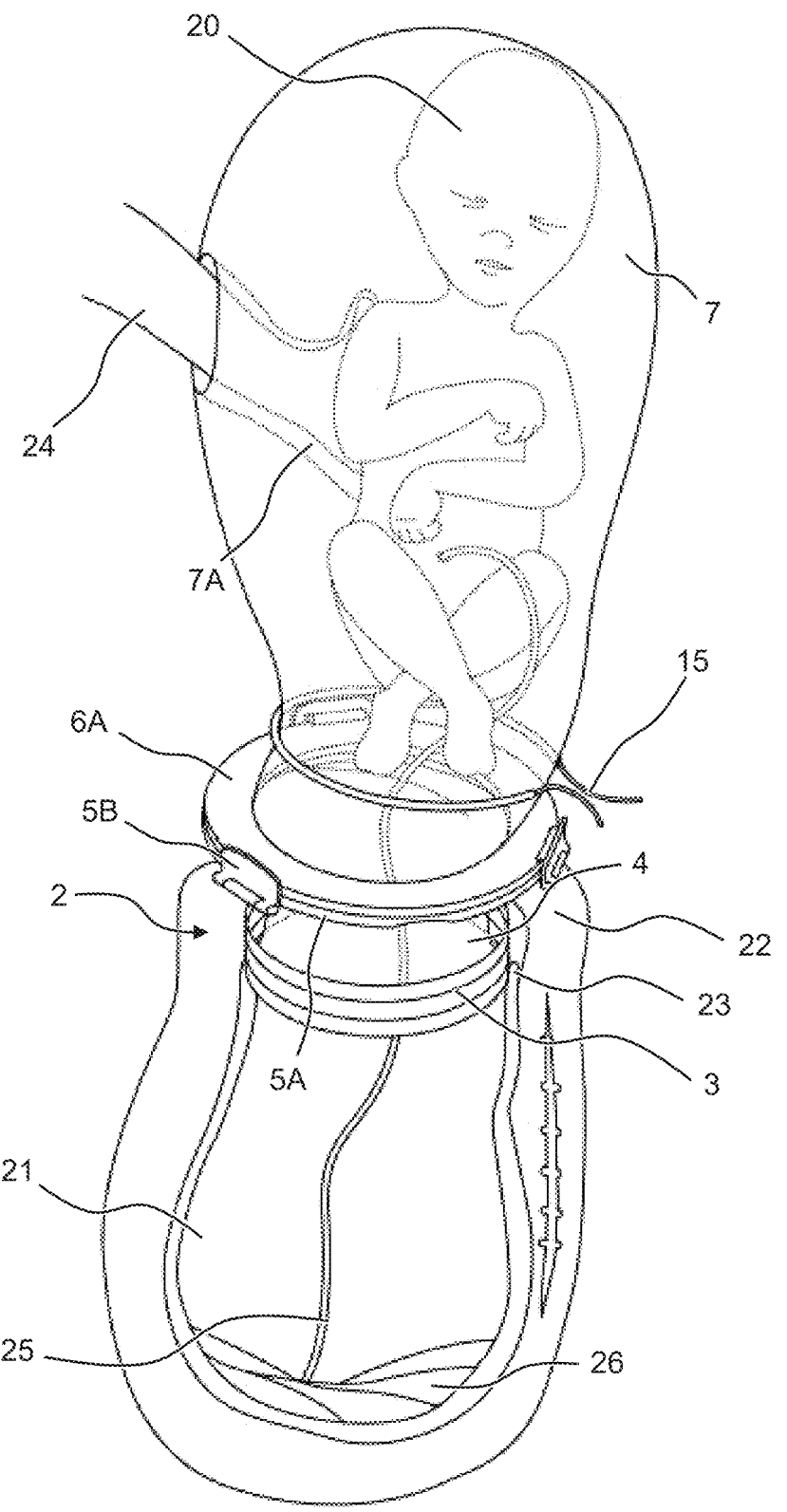
Figure 3F:
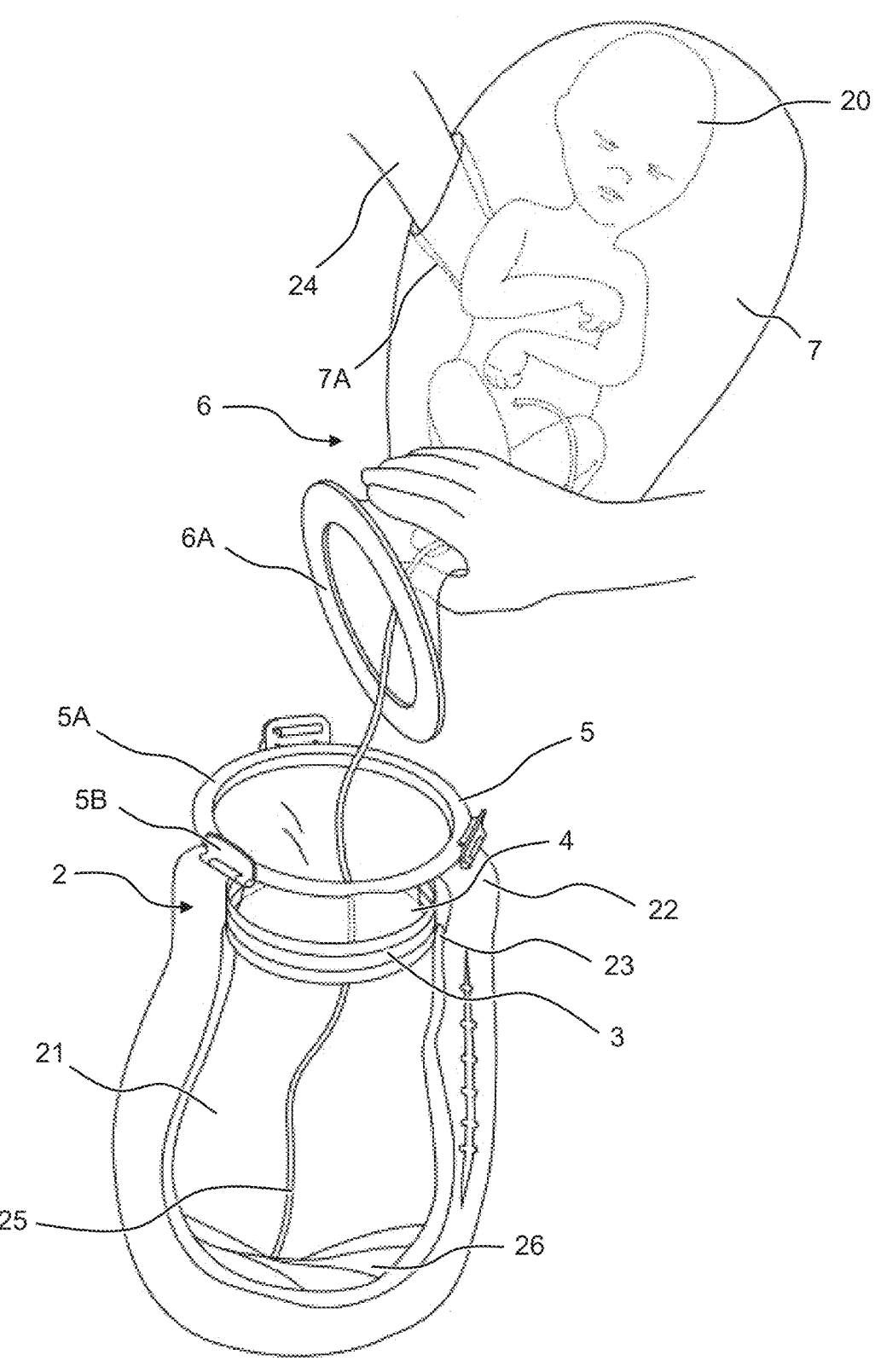
Figure 3G:
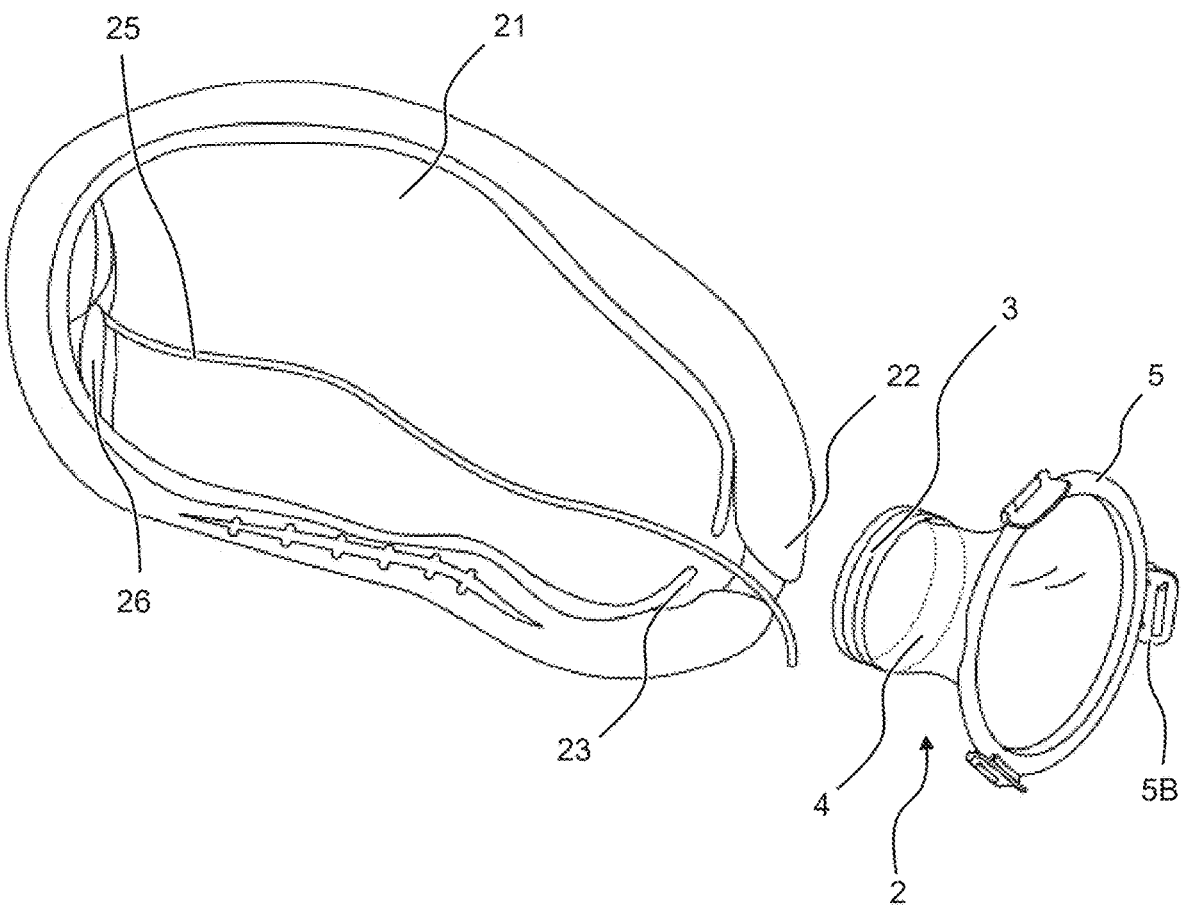

A detailed cross-sectional view of the coupling member 6A of the transfer device 6 and the base body 5A of the base device 5 is shown in FIG. 2. Here the base body 5A is the lower rigid ring provided with clips 5B. The base body 5A cooperates with the coupling member 6A by form-fittingly connecting to the coupling member 6A. In order to provide a reliable connection between the coupling member 6A and the base body 5A, the coupling member 6A is provided with a sealing circumferential flexible O-ring 10A and a labyrinth closure 10B provided in a recess of the coupling member 6A.

FIG. 3 provides schematical view of the method of transferring a preterm baby 20 from the natural womb 21. First (FIG. 3A), the birth canal retractor 2 is placed in the birth canal 22 wherein the insertion ring 3 is positioned such that the birth canal retractor 2 abuts the cervix 23. FIG. 3A further shows the retractor sleeve 4 and the base device 5 provided with clips 5B. Secondly, during the cervical dilation phase (FIG. 3B) the diameter of the insertion ring 3 is inherently, manually or automatically increased. The progress of the dilation can still be checked by hand by, for example, the medical practitioner (not shown). Subsequently, when cervical dilation is sufficient for delivery of the preterm baby, the transfer device 6 is releasably secured to the base device 5 (FIG. 3C). FIG. 3C further shows the clips 5B, coupling member 6A, transfer bag 7 and glove 7A integrated in the transfer bag 7. In FIG. 3D the preterm baby 20 is transferred from the natural womb 21 via the birth canal retractor 2 into the transfer bag 7 of the transfer device 6 by assistance of the hand 24 of the medical practitioner received in the integrated glove 7A. Once the preterm baby 20 is fully transferred into the transfer bag 7, the transfer device 6 can be detached from the birth canal retractor 2, by unclipping the base body 5A of the base device 5 from the coupling member 6A of the transfer device 6 as shown in FIG. 3E. Once the transfer device 6 is detached from the base device 5 (FIG. 3F) the transfer bag 7 can be placed onto a transfer station (not shown) for canulation of the umbilical cord 25 still connected to the preterm baby 20 and the natural placenta 26 located in the natural womb 21. After canulation of the umbilical cord 25 and connecting the canulated umbilical cord 25 to an artificial placenta (not shown), the birth canal retractor 2 is removed from the birth canal 22 (FIG. 3G). Although not shown in FIG. 3G, the insertion ring 3 is preferably first deflated before removal.

Figure 4:
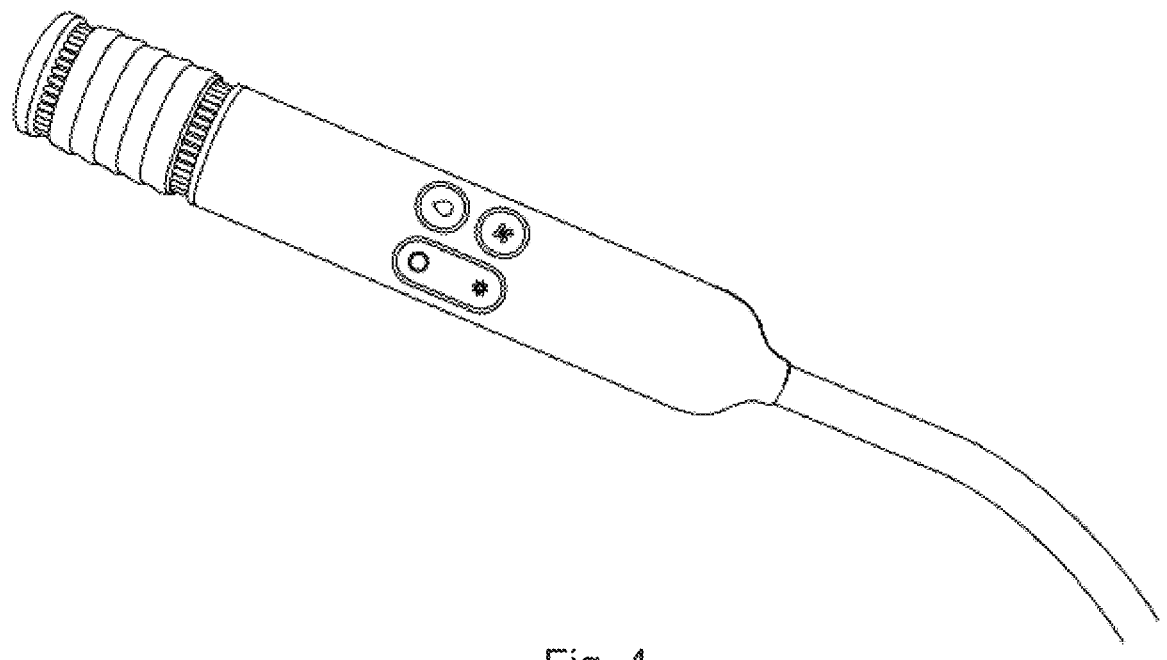
FIG. 4 shows a transfer device according to the sixth aspect of the invention.
Figure 5:
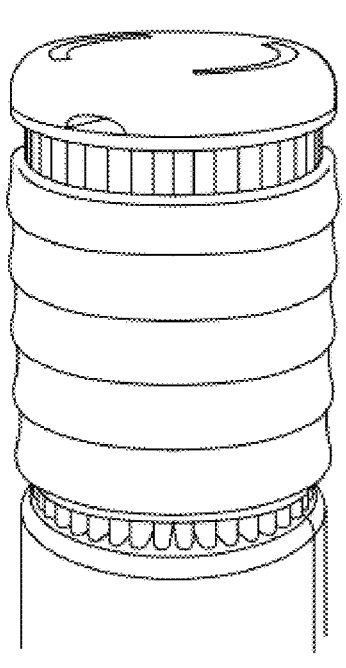
FIG. 5 shows a detailed part of the transfer device according to the sixth aspect of the invention.
Figure 6:
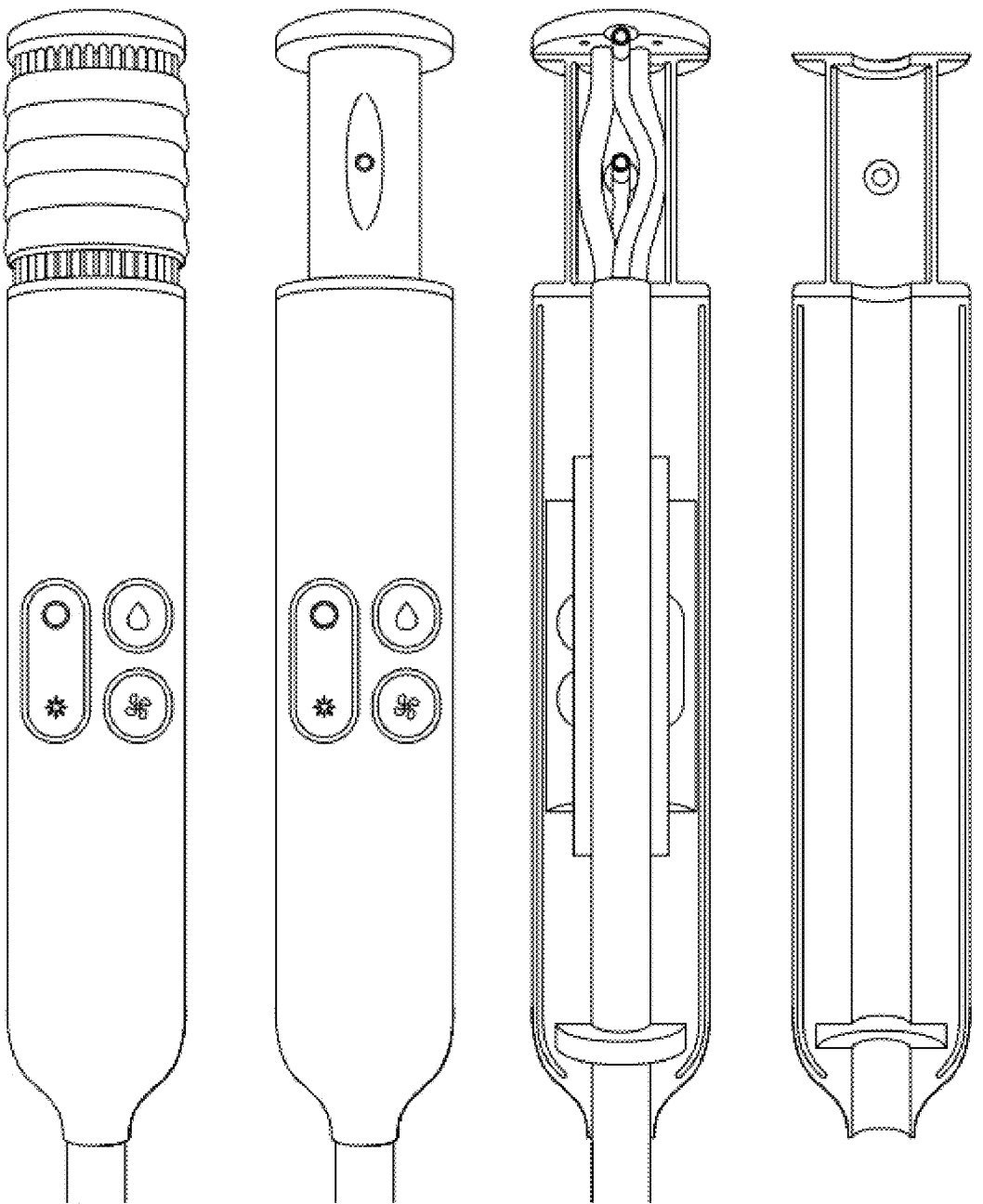
FIG. 6 shows the different parts of the transfer device according to the sixth aspect of the invention.

FIGS. 4, 5 and 6 show an assembled transfer device according to the alternative embodiment of the present invention comprising the transfer device and the expandable ring. The transfer bag (connected to the expandable ring) is not shown in FIGS. 4 and 5. The head of the transfer device has two slits for inserting artificial amniotic fluid into the expanded biobag. The two slits to the right of the amniotic fluid slits in FIG. 6 are for inserting heated air into the bumper part of the double walled biobag. At the right side of the transfer device, control buttons and the main supply tubes are located. The main supply tube holds low voltage electric control wires, air supply and amniotic fluid supply and removal tubes. The other end of the main supply tube is attached to power supply unit(s), plus a control—and a monitoring device (not shown). The expandable ring (FIG. 5), is equipped with wedges to, when expanded in the birth channel, maintain a fixed position in this birth channel.

Figure 7:
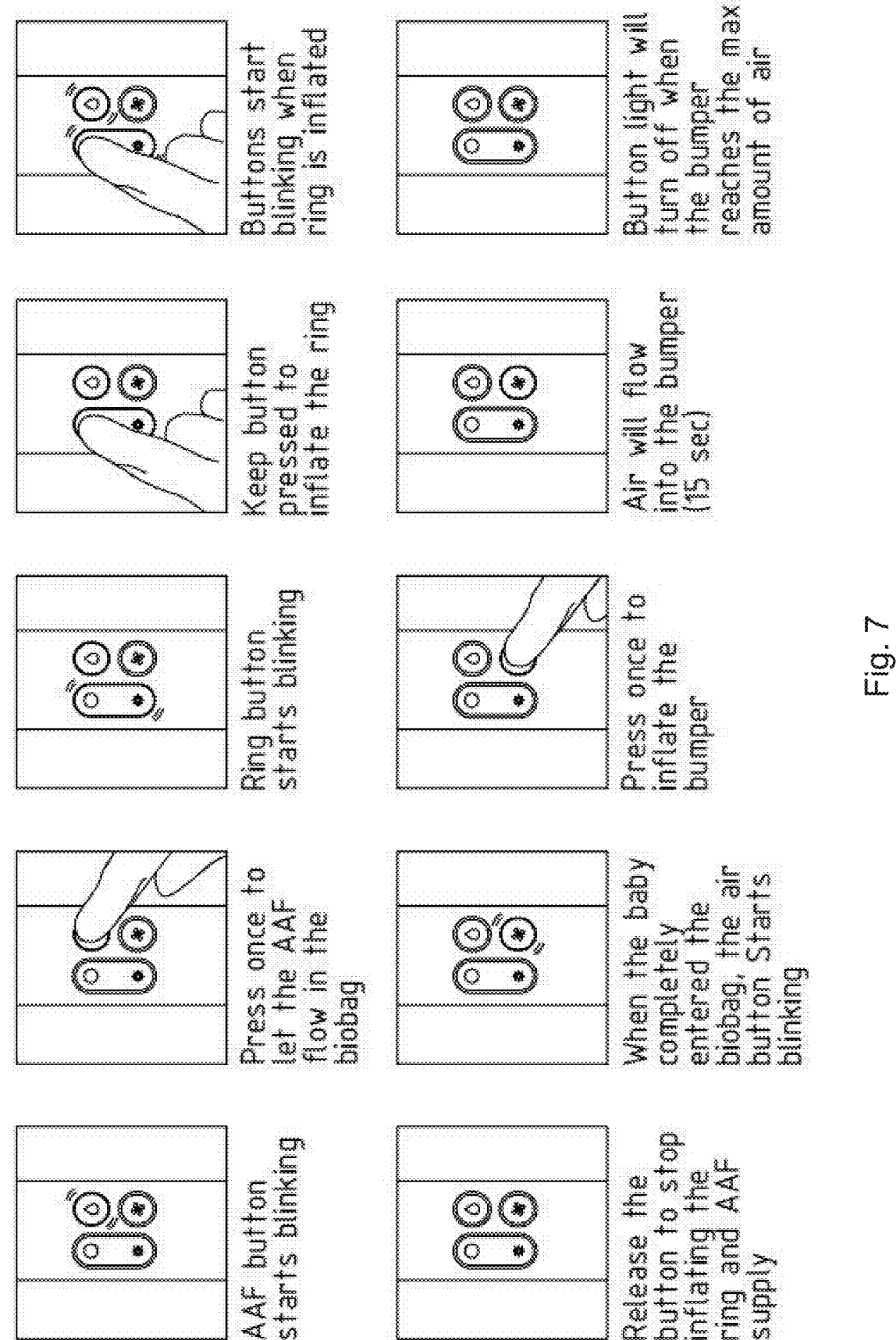
FIG. 7 is a brief guideline on the use of the transfer device according to the sixth aspect of the invention.

FIG. 7 shows the buttons and their functions on the transfer device according to the alternative embodiment of the present invention. At the beginning of the process, i.e.

after the transfer device is inserted in the birth canal, the artificial amniotic fluid (AAF) button starts blinking. After pressing once, the artificial amniotic fluid flows into the biobag. Subsequently the ring button starts blinking. By pressing (and holding) the ring button, the ring inflates. By the time the ring is inflated to the full extend the buttons starts blinking. In order to stop the inflation of the ring and supply of the artificial amniotic fluid, the ring button is released. Once the preterm baby completely entered the transfer bag (also referred to as biobag) the air button starts blinking. By pressing the air button the bumper is inflated. During 15 seconds air will flow into the bumper closing the transfer bag. By the time the bumper reaches the maximum amount of air, the air button light will turn off.

Figure 8:
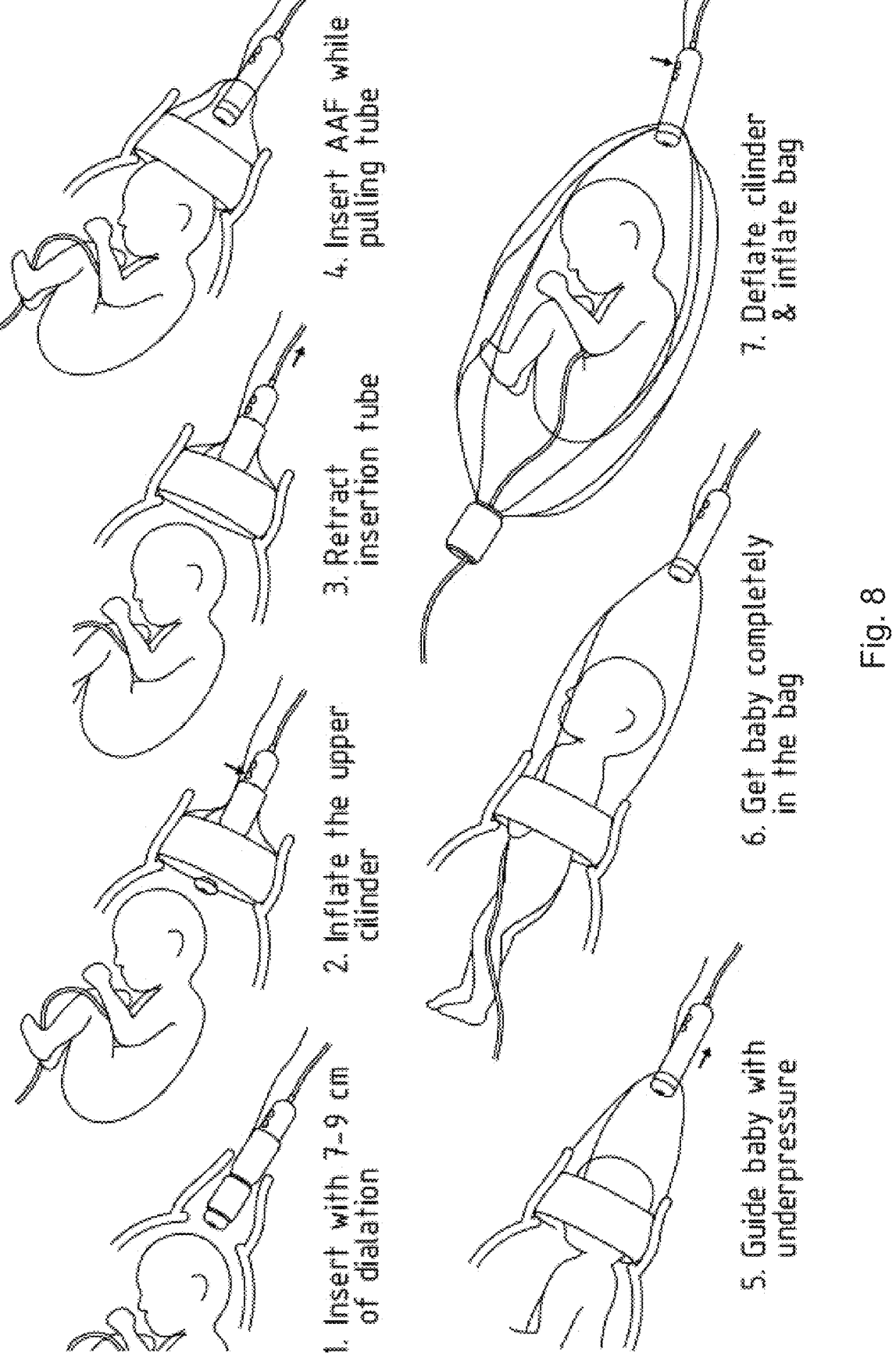
FIG. 8 depicts the method of transferring a preterm baby from the natural womb into the transfer bag according to the seventh aspect of the invention.

FIG. 8 shows the method of the present invention using the alternative transfer device. In order to provide the transfer device shown in FIG. 9, a folded double layer biobag (the light blue part in FIG. 9, point 1) is attached at the top of the device, inserted under the expandable ring (the green part in FIG. 9), and at the other end the (folded) biobag is attached at the right part of the expandable ring. Before insertion of the transfer device, the birth channel may be disinfected. The sterile transfer device, consisting of a cylindrical control rod (base body) with as attachments a collapsed double layer biobag and an expandable ring, is inserted into the vagina when the mother has between 7-9 cm of dilatation. The device is positioned such in the vagina that the expandable ring, after full expansion, generates an access gate to the attached biobag. The biobag is on one side attached to the cylindrical rod an on the other side to the inflatable ring. Subsequently, the upper cylinder (the ring) is inflated. The expansion of the ring in the birth channel, together with the surface structures in the outside of the ring, fixates the ring relative to the birth channel. After the full expansion of the expandable ring, the insertion tube of the transfer device is (partially) retracted from the birth canal, thus increasing the filled volume of the biobag which generates a slightly lower environmental pressure in the biobag. Simultaneously, artificial amniotic fluid is inserted into the transfer device while pulling the insertion tube of the transfer device. The perinate (preterm baby) is then, due to the slightly lower environmental pressure in the biobag, the maternal contractions plus the maternal all-fours position, slowly transferred into the biobag. After the baby is completely inside the biobag, i.e. 'born' into the biobag, and for at least the larger part thereof outside the birth channel as can be understood from FIG. 9, the expandable ring is de-expanded (e.g. deflated). The diameter of the expandable ring after de-expansion is such that the flows in the umbilical cord, which then goes through the hole in the expandable ring, are not occluded. The whole device, including the inside the biobag captured perinate, is then removed from the birth channel. Next the outer wall of the double-walled (double-layer) biobag is, through the tubing in the cylindrical control rod, inflated with sterilized air, for additional thermal insulation and protection of the baby in the bag while keeping the weight of the bag low. If necessary extra sterilized artificial Amniotic fluid is inserted through the tubing in the control rod into the inner part of the biobag.

What is claims is:

1. A transfer assembly for transferring a preterm baby from a natural womb of a pregnant mammal to a transfer bag, the assembly comprising:
    a base device comprising an annular shaped pass-through opening having a central axis, wherein the pass-through opening is configured to allow the preterm baby to pass through the base device, and wherein the base device further comprises a womb facing side and a transfer bag facing side; and
    a transfer device comprising the transfer bag, said transfer bag being a flexible bag provided with an annular shaped opening having a central axis, wherein the annular shaped opening is configured to allow the preterm baby to be received in the transfer bag, and wherein the annular shaped opening is further provided with a coupling member, which coupling member is releasably secured to the transfer bag facing side of the base device in such configuration that the central axis of said pass-through opening coincides with the central axis of said annular shaped opening,
    wherein the womb facing side of the base device is connected to a birth canal retractor, said birth canal retractor comprises a flexible sleeve disposed in a cylindrical configuration between the womb facing side of the base device and an adjustable access ring, wherein the birth canal retractor is arranged to be inserted into the birth canal of the pregnant mammal at least with the access ring thereof,
    wherein the access ring is configured to be expanded or inflated while in the birth canal, thereby providing an access for the preterm baby to the transfer assembly through the access ring in an expanded or inflated state of the access ring, and
    wherein the transfer bag is provided with at least one integrated glove for receiving the hand of a medical practitioner in order to allow the medical practitioner to transfer the preterm baby from the natural womb into the transfer bag.

2. The transfer assembly according to claim 1, wherein the womb facing side of the base device and the birth canal retractor forms one integral birth canal retractor device.

3. The transfer assembly according to claim 1, wherein the birth canal retractor is arranged to be inserted into the birth canal of the pregnant mammal at least with the access ring and a substantial part of the flexible sleeve.

4. The transfer assembly according to claim 1, wherein the base device and/or the transfer device further comprises an inlet for supplying artificial amniotic fluid (AAF) to the interior of the transfer assembly.

5. The transfer assembly according to claim 1, wherein the transfer bag is further provided with a valve to release air from the transfer bag to the exterior.

6. The transfer assembly according to claim 1, wherein the integrated glove is positioned opposite to the annular shaped opening of the transfer bag.

7. The transfer assembly according to claim 1, wherein the transfer bag further comprises an integrated wire to close the annular shaped opening of the transfer bag after the preterm baby is received in the transfer bag, wherein the closure of the annular shaped opening of the transfer bag is facilitated by loosely securing the integrated wire around the umbilical cord connected to the preterm baby.

8. A kit for assembling a transfer assembly for transferring a preterm baby from a natural womb of a pregnant mammal to a transfer bag, the kit-of-parts comprising:
    a base device comprising an annular shaped pass-through opening having a central axis, wherein the pass-through opening is configured to allow the preterm baby to pass through the base device, and wherein the base device further comprises a womb facing side and a transfer bag facing side; and
    a transfer device comprising the transfer bag, said transfer bag being a flexible bag provided with an annular shaped opening having a central axis, wherein the annular shaped opening is configured to allow the preterm baby to be received in the transfer bag, and wherein the annular shaped opening is further provided with a coupling member, which coupling member is configured to be releasably secured to the transfer bag facing side of the base device in such configuration that the central axis of said pass-through opening coincides with the central axis of said annular shaped opening, wherein the transfer bag is provided with at least one integrated glove for receiving the hand of a medical practitioner in order to allow the medical practitioner to transfer the preterm baby from the natural womb into the transfer bag.

9. The kit according to claim 8, the kit further comprising:
a birth canal retractor configured to be connected to the womb facing side of the base device, said birth canal retractor comprises a flexible sleeve disposed in a cylindrical configuration between a first open end connectable to the womb facing side of the base device and a second open end provided with an adjustable access ring, wherein the birth canal retractor is arranged to be inserted into the birth canal of the pregnant mammal at least with the access ring thereof,
wherein the access ring is configured to be expanded or inflated while in the birth canal, thereby providing an access for the preterm baby to the transfer assembly through the access ring in an expanded or inflated state of the access ring.

10. The kit according to claim 8, wherein the base device further comprises a birth canal retractor connected to the womb facing side of the base device, said birth canal retractor comprises a flexible sleeve disposed in a cylindrical configuration between the womb facing side of the base device and an adjustable access ring, wherein the birth canal retractor is arranged to be inserted into the birth canal of the pregnant mammal at least with the access ring thereof, and wherein the access ring is configured to be expanded or inflated while in the birth canal, thereby providing an access for the preterm baby to the transfer assembly through the access ring in an expanded or inflated state of the access ring.

11. A method for transferring a preterm baby from a natural womb of a pregnant mammal to a transfer bag, the method comprising the steps of:
i) providing a kit according to claim 9;
ii) providing an pregnant mammal;
iii) performing lavage of the birth canal of the pregnant mammal;
iii) inserting the birth canal retractor connected to the base device into the birth canal of the pregnant mammal at least with the access ring thereof;
iv) monitoring a cervical dilation of the pregnant mammal and simultaneously increasing the diameter of the access ring while in the birth canal such that it eventually provides an access for the preterm baby to the transfer assembly;
v) in case sufficient cervical dilation is observed, releasably securing the transfer device to the base device to form a transfer assembly;
vi) supplying artificial amniotic fluid (AAF) to an interior of the transfer assembly;
vii) allowing a medical practitioner to access the natural womb by hand using the integrated glove provided in the transfer bag; and
viii) transferring the preterm baby from the natural womb into the transfer bag.

12. The method according to claim 11, wherein the transfer bag comprises an integrated wire in the vicinity of the annular shaped opening, the method further comprises the step of:
closing the annular shaped opening of the transfer bag by loosely securing the integrated wire of the transfer bag around the umbilical cord connected to the preterm baby.

13. The method according to claim 11, wherein the method further comprises the step of:
releasing the transfer device from the base device and placing the transfer bag on a horizontal plane such that the annular shaped opening of the transfer bag is facing upwards away from the horizontal plane.

* * * * *